United States Patent [19]

Bon et al.

[11] Patent Number: 4,592,810
[45] Date of Patent: Jun. 3, 1986

[54] ELECTROCATALYTIC PRODUCTION OF 2,3,5,6-TETRACHLOROPYRIDINE FROM PENTACHLOROPYRIDINE

[75] Inventors: Charles K. Bon, Concord; Arthur J. Kamp, Oakley; Theodore J. Sobieralski, Antioch, all of Calif.

[73] Assignee: The Dow Chemical Company, Midland, Mich.

[21] Appl. No.: 712,936

[22] Filed: Mar. 18, 1985

[51] Int. Cl.$^4$ ............................................. C07D 213/61
[52] U.S. Cl. ................................. 204/59 R; 204/73 R
[58] Field of Search ............................ 204/59 R, 73 R

[56] References Cited

U.S. PATENT DOCUMENTS 3,694,332  9/1972  Parker ................................ 204/73 R

FOREIGN PATENT DOCUMENTS 1499650  2/1978  United Kingdom .

OTHER PUBLICATIONS

*Organic Electrochemistry* 2nd Ed. Baizer Editor Marcel Dekker N.Y. (1984), p. 261.

*Primary Examiner*—John F. Niebling
*Attorney, Agent, or Firm*—Robert R. Stringham

[57] ABSTRACT

2,3,5,6-Tetrachloropyridine is obtained in high selectivity and yield by the electrocatalytic reduction at a stainless steel cathode of pentachloropyridine in an aqueous acetonitrile solution containing zinc chloride. Chlorine or oxygen may be co-produced at the anode.

11 Claims, No Drawings

ELECTROCATALYTIC PRODUCTION OF 2,3,5,6-TETRACHLOROPYRIDINE FROM PENTACHLOROPYRIDINE

BACKGROUND OF THE INVENTION 2,3,5,6-Tetrachloropyridine (symmetrical tetrachloropyridine—"sym-tet", henceforth) is an important intermediate for the preparation of several commercial pesticides. A variety of methods of preparing it are known; these methods preponderantly involve chemical or electrolytic reduction of pentachloropyridine ("PCP" hereinafter). None of the known methods are "electrocatalytic", as the term is used here.

All electrochemical reactions are catalytic in a sense, since the primary step, the electron exchange, is "catalyzed" by the electrode. Some electrochemical reactions involve the formation of a reactive intermediate species in this step, such as nascent hydrogen—for example, which then reacts chemically with the substrate, as by reduction, for example. If the source material for the reactive species is not regenerated in the cell, the overall process is better described as indirect electroreduction (or oxidation) than as electrocatalytic. Here, the term electrocatalytic is reserved for processes which may be rationalized as involving the formation of a reactive species from a source material ($Zn^{2+}$) which is regenerated in the course of the overall reaction.

Of the several known types of chemical reductions of PCP to sym-tet, the one most relevant to the present invention is the use of zinc metal in acidic media. British Pat. No. 1,499,650 is directed to such a process wherein a mixture of PCP, zinc particles, HCl and water is heated to a temperature of 110°-160° C. under at least autogenous pressure. The reaction is described in the patent as reduction of the PCP by nascent hydrogen generated by the reaction of the zinc with the acid. The highest reported yield of sym-tet, equivalent to 91.4% based on PCP charged, was obtained at a PCP conversion of 98.8%. A total of about 5% of di- and trichloropyridines and about 1% of an isomeric tetrachloropyridine were co-produced.

U.S. Pat. No. 4,259,495 is directed to another chemical method in which PCP is reduced with from 1.1 to 1.3 gram atoms of zinc per mole of the PCP in a mixture of a phosphonate or phosphate ester and a solution in water of about 2-3 moles/liter of an ammonium salt, such as ammonium carbonate, ammonium salts of phosphonomonoesters, ammonium sulfate and ammonium chloride. The reaction is carried out at temperatures of 60°-120° C. under ambient pressures. It is stated that sym-tet can be obtained, 97% pure, in 92% of theoretical yield. PCP conversions of up to about 99% and trichloropyridine contents as low as about 1% are attained.

Electrolytic reductions of PCP to sym-tet are disclosed in two U.S. patents. U.S. Pat. No. 3,694,332 is directed to the use of mercury, lead, iron, tin or zinc cathodes for the reduction of PCP dissolved in an alcohol, a cyclic or acyclic ether, a glycol monoether, a lower amide or sulfolane. A neutral or acidic salt such as sodium or ammonium tosylate, acetate, chloride or fluoride or a free acid such as acetic acid, HCl or $H_2SO_4$ is used as the electrolyte. The reaction product obtained at a stirred mercury cathode from a solution of PCP in dimethoxyethane and methanol, using 30% $H_2SO_4$ as the electrolyte, in a period of 129 minutes at 25° C. (current efficiency 88%), consisted of trichloropyridines (2.7%), sym-tet (97.3%) and a trace of PCP.

U.S. Pat. No. 4,242,183 discloses the use of a particularly active type of silver cathode to reduce PCP to sym-tet (or to 2,3,5-trichloropyridine). Yields of up to about 90% of the sym-tet can be attained, without substantial further reduction, if the reaction is stopped after about 96% of the PCP has been converted. The reduction is carried out in a basic, aqueous catholyte comprising an organic solvent such as THF, dioxane, lower alcohols, glycol ethers, sulfolane and lower amides. A porous separator is used to divide the cell into separate cathode and anode compartments, the latter being charged with an aqueous base. A cathode potential of about −1.1 volts (relative to a saturated calomel electrode) is preferred for sym-tet production; about −1.3 volts is preferred for 2,3,5-trichloropyridine production. Temperatures of about 20°-35° C. are preferred.

An electrocatalytic method of converting a vicinal dihalo-ethane or -propane to the corresponding ethylene or propylene and the elemental halogen(s) is disclosed in U.S. Pat. No. 4,162,948. A divided cell is used. The catholyte contains the dihalo compound, water, zinc chloride and a detergent. The anolyte (composition not disclosed) presumably consists of $ZnCl_2$ and water. The dehalogenation is said to be operable at temperatures of from 0°-100° C.; examples at 40° and 60° are given. The electrolytic reaction disclosed is the decomposition of the $ZnCl_2$ to metallic zinc (at the cathode) and chlorine (at the anode). The zinc chloride (or at least a zinc dihalide) is regenerated (or formed) as a product of the chemical dehalogenation reaction between the adjacent halogen substituents on the dihaloalkane and the metallic zinc. This process, like the classical coupling reaction between 2 molecules of a monohalocompound and a metal, does not result in replacement of a halosubstituent by hydrogen. (The coupling type of reaction is known to occur when 4-halo-2,3,5,6-tetrafluoropyridines are electroreduced in aprotic media: Chambers, Clark, Sargent and Drakesmith, *Tetrahedron Letters*, 21, p. 1917 (1979)).

Essentially the same system can be employed, according to Pletcher, Razaq and Smilgin; *Jour. Appl. Electrochem.*, 11, (1981) 601–603, to effect either the conversion of 1,1,2-trichloroethane to vinyl chloride or of nitrobenzene (as such or as the 2-fluoro derivative) to aniline (or 2-fluoroaniline). The use of a two-phase system (i.e., an emulsion) is said to have permitted attainment of current densities greater than 0.5 A/cm². The presence of HCl in amounts up to 7M did not adversely effect current efficiency for zinc deposition (in a preliminary experiment involving no organic substrate). Again, neither reaction results in replacement of a halosubstituent by hydrogen or removal of a halo substituent from an aromatic (carbocyclic or heterocyclic) ring.

All of the foregoing methods of reducing PCP to sym-tet leave something to be desired, in one respect or another. The chemical methods of the British '650 patent and the U.S. '495 patent result in production of a zinc salt waste stream, which must be disposed of in an environmentally acceptable manner. The electrolytic method of the U.S. '332 patent requires, for really good results, the use of a mercury or lead cathode. Use of these metals, especially mercury, in electrolytic processes, without contaminating the environment, has been found by industry to be difficult. The electrolytic method of the U.S. '183 patent requires the use of an expensive (silver) cathode material which must be cleaned with acid (at the expense of some loss of silver) and reactivated (by anodization) frequently.

The electrocatalytic reactions described above are said, by Pletcher et al, to be illustrative of what can be done by electrocatalysis. However, which specific reactions of other types are and are not amenable to this approach is not indicated. Those familiar with the great and often unpredictable sensitivity of electrochemical systems to small differences in materials and conditions will appreciate that the foregoing prior art falls short of suggesting that electrocatalysis is a feasible alternative to the known electrolytic methods for reducing PCP to sym-tet. (With regard to the latter sensitivity, see *Basics of Electroorganic Synthesis*, D. K. Kyriacou, John Wiley & Sons, N.Y., N.Y. 1981; pp. 20, 22, 28, 54, 69, 82, 92, 102–4, 112–117, 125, 133 and 134.)

The higher current densities said by Pletcher et al to be attainable with reaction media which are emulsions are desirable but it is well known (Kyriacou, loc. cit., p. 16) that emulsions give trouble in divided cells (which would appear to be indicated for a process involving formation of zinc at the cathode and of chlorine at the anode). Efficient operation with emulsions also imposes considerably higher stirring requirements.

OBJECTS OF THE INVENTION

The primary object of the present invention is to provide a method of preparing sym-tet from PCP which does not have the above-identified shortcomings of the known methods.

A corollary object is to extend the utility of electrocatalysis to the selective replacement by hydrogens of the chlorine in the 4-position of PCP.

Another object is to be able to carry out the electrocatalytic reduction of PCP at only moderately elevated temperatures and at ambient pressures in a single-phase aqueous medium.

Still other objects will be made apparent to those knowledgeable in the art by the following specifications and claims.

SUMMARY OF THE INVENTION

It has been found that the foregoing objects can be attained by use of an aqueous catholyte in which the PCP solvent is or has the essential characteristics of acetonitrile, for the electrocatalytic reduction of PCP with zinc.

The invention may be more narrowly defined as the electrocatalytic method for preparing sym-tet from PCP which comprises:

a. providing an electrolytic cell having a cathode and an anode, b. charging to said cell as the catholyte a solution comprising said PCP, water, $ZnCl_2$ or $ZnBr_2$, a solvent which is or has the essential characteristics of acetonitrile, a non-basic supporting electrolyte and, optionally, an acid source material, c. charging to said cell as the anolyte a solution comprising a water-miscible solvent, water, a non-basic, supporting electrolyte and, optionally, an acid source material, d. heating the cell contents as necessary to establish the temperature therein at a value within the range of from about 25° to about 100° C., e. applying across said cell a D.C. potential such to establish and maintain a cathode potential of from about $-2$ to about $-1$ volts, for a period of time as required to attain a desired degree of conversion of the PCP charged;

said cathode consisting of an inert, electroconductive material at which $Zn^{2+}$ can be reduced at said cathode potential to $Zn^0$; said anode consisting of an inert, electroconductive material at which $Cl^-$ and/or $Br^-$ ions can be oxidized to a halogen which is $Cl_2$, $Br_2$ or $BrCl$, or at which water or "hydroxyl ions" can be oxidized, thereby liberating oxygen.

The cell of course can be adapted as may be necessary to largely prevent contact of said halogen or oxygen with said $Zn^0$ and/or oxidation of sym-tet (or other chloropyridine species) at the anode.

The cathode potential is that relative to a saturated calomel electrode or other standard reference electrode and is determined with conventional means, such as a properly positioned Luggin capillary connected to the reference cell.

Preferably, the cell is divided by a suitable membrane or diaphragm into separate anode and cathode compartments, the zinc halide is $ZnCl_2$, the electrolyte is a tetrafluoroborate, the solvent component of the anolyte is $CH_3CN$, the reaction temperature is about 70°–80° C., the cathode material is stainless steel and the anode material is titanium coated with ruthenium oxide.

DETAILED DESCRIPTION

The cell employed may be divided into separate compartments by a membrane having the requisite ion-transport properties or by a porous member, such as a sintered ceramic diaphragm which limits mass transfer between the two compartments. Alternatively, the anode may be surrounded by an inverted cup or a similar means which affords contact between the anolyte and catholyte at a low level in the cell and is adapted for gas ($Cl_2$ or $O_2$, for example) takeoff above the anolyte.

The zinc halide preferably is $ZnCl_2$ but may be $ZnBr_2$ and is employed in an amount such as to ensure having an adequate $Zn^{2+}$ activity in the vicinity of the cathode. For efficient operation of the cell, the halide is used in an amount such as to provide about 2 to 4 gram equivalents of $Zn^{2+}$ per g. mole of PCP present in the cell. Larger amounts, up to the point where inadequate PCP solubility results, may be employed but are not seen to offer any advantage.

The supporting electrolyte is considered essential to minimizing the IR drop across the cell, which determines the cell voltage required to establish the desired cathode potential. It must dissolve and dissociate to a sufficient extent in the aqueous catholyte and/or anolyte to provide an adequate supply of current carrying ions. Neutral or acidic salts, such as alkali metal, ammonium, substituted ammonium and phosphonium salts of organic or mineral acids are preferred for this purpose. Exemplary of such salts are ammonium acetate, ammonium chloride, tetra(n-butyl)ammonium perchlorate, sodium tetrafluoroborate, potassium nitrate, lithium perchlorate, tetraethyl ammonium tetrafluoroborate and tetramethyl phosphonium chloride. The electrolyte may be introduced as a base, such as $NH_4OH$, for example, provided that an acid source material is also employed, in an amount at least sufficient to neutralize the base.

Free acids, such as HCl, for example, will generally be employed primarily as acid source materials but can also function as electrolytes.

The supporting electrolyte is employed in amounts, up to the saturation level (0.4–0.5 molar, for example), such that its concentration in the catholyte or anolyte is generally at least 0.1 molar.

It has been found essential to attainment of the objects of the invention to employ, as the PCP solvent in the catholyte, one having the essential characteristics of acetonitrile. $CH_3CN$ itself is preferred but other non-protic, water-miscible liquids having atmospheric boiling points of about 70° or higher and dielectric constants of about 35 or more should be suitable. The solvent of course should be inert, i.e., not detrimentally reactive to an intolerable degree.

The choice of the solvent component of the anolyte is less critical, but a solvent which is or has the essential characteristics of acetonitrile is highly preferred. When an undivided cell is used, the catholyte and anolyte have substantially the same compositions and $CH_3CN$ per se is highly preferred.

The objects of the invention may be attained at reaction temperatures of from about 25° to about 100° C. At temperatures below 25° the reaction rate is quite low and at temperatures above the atmospheric boiling point of the PCP solvent (~82° C. @ 760 mmHg for $CH_3CN$) resort to operating pressures greater than atmospheric will be necessary. At temperatures approaching 100° C., these pressures become high enough to considerably increase plant costs.

Addition of an acid source material would appear to be necessary if the requisite $H^+$ for the reaction is abstracted from water (as by a carbanion generated at the cathode) and $Cl^-$, rather than $OH^-$, is oxidized at the anode. That is, if this results in $OH^-$ accumulation, it should be unfavorable to the desired reduction. However, it has been found that such addition is not necessarily required (see Example 2 herein). Whether this is because zinc deposits as a layer, however thin, on the cathodic electrode and simply acts as a more active "catalyst" for electrolytic reduction of PCP is not known. Better current efficiencies and better selectivity result if an acid source material is employed and this practice is therefore preferred.

The acid source material, when used, ordinarily will be added in amounts of from about 1 to about 4, preferably about 2, g. moles per g. mole of PCP to be converted. When it is HCl or a chloride, it can also ensure a higher $Cl^-$ activity in the anolyte.

The cathode material (which may constitute the entire cathodic electrode or only a surface coating thereon) should be inert, i.e., not chemically reactive with the catholyte to an intolerable extent, and adequately electroconductive. It is highly desirable that hydrogen formation does not occur at the cathode, but this does not necessarily require use of a cathode material having a high hydrogen overvoltage. That is, so long as the cathode surface is, in effect, at least, pre-empted by deposition of zinc—which has a high hydrogen overvoltage—a cathode material at which hydrogen would otherwise tend to form can be employed. Stainless steel, for example, has been found eminently suitable as a cathode for the electrocatalytic reduction of PCP to sym-tet. It has been observed that the reduction of the PCP does not go at this cathode in the absence of the zinc halide. However, zinc will deposit on the stainless steel in the absence of PCP. Whether or not even transient deposition occurs in the presence of PCP has not been established but at least it has been found that this type of cathode is not substantially heavier after the reaction than it was initially.

The present invention of course is not predicated on a correct understanding of the reaction mechanism. The emperical fact is that $Zn^{2+}$ mediates the requisite electron transfer in such a manner that a high degree of PCP conversion is attained without substantial further reduction of the sym-tet produced.

Other specific cathode materials believed to be suitable are zinc, cadmium, zinc/cadmium alloys, aluminum or even mercury (as such or as a zinc amalgam), although mercury is generally environmentally objectionable.

Cathode potentials within the range of from about $-2$ to about $-1$ volts are considered suitable; the range of from about $-1.45$ to $-1.25$ volts is preferred and the range of about $-1.3$ to about $-1.4$ volts is most preferred.

Exemplary of anode materials other than ruthenium-coated titanium which are believed suitable are generally those employed in cells operated for chlorine or chlorates production. Still others are graphite, noble metals, such as platinum and gold; and metal oxides, particularly when operating the present process under conditions favorable to $O_2$ formation at the anode.

Work-up of the reduction mixtures formed in the practice of the present invention can be by any conventional method for such mixtures but suitably is carried out by adding a higher boiling, water-immiscible solvent, such as perchloroethylene, neutralizing any acid present, washing with water to extract the inorganics (and a substantial portion of the $CH_3CN$) and fractionally distilling the organic phase to separate the polychloropyridines from the rest of the $CH_3CN$ and from each other. The $CH_3CN$ and zinc halide components can be recovered from the aqueous extract by conventional procedures which will be apparent to those knowledgeable in the art.

The relative amounts of water and $CH_3CN$ in the catholyte or anolyte are conveniently expressed as the wt. % water in the "wet $CH_3CN$". This can range from about 1% up to a water content such that PCP solubility (in the catholyte) is depressed to an intolerable extent. In one experiment (Example 2 herein) the content of water in the $CH_3CN$ component of the catholyte was 20 wt. % and good results were still obtained. In general, a content of from about 3 to about 25 wt. % $H_2O$ in both the catholyte and anolyte is preferred. A more preferred range is from about 5 to about 15 wt. % $H_2O$. At low initial water contents, it may be necessary to add some water as the reaction progresses, particularly if oxygen is evolved at the anode.

The relative amounts of PCP and $CH_3CN$ employed are such that the % PCP in the (wet) $CH_3CN$ is within the range of from about 1 wt. % up to the level at which sym-tet begins to appear as a separate phase in the catholyte as the reduction proceeds.

To favor halogen, rather than $O_2$, production at the anode, the supporting electrolyte (or the acid source material) may comprise a halide. Preferably, the halide is added as a hydrogen halide, as the reaction progresses. A halogen acid or protic ammonium salt may be used instead, in an amount less than that which results in formation of a separate brine phase.

EXAMPLES

The following examples are for purposes of illustration and are not to be construed as limiting the present invention in a manner inconsistent with the claims in this patent.

EXAMPLE 1

(Hydrochloric Acid Added During Reaction)

A divided beaker cell was equipped with a platinum anode, a 316 stainless steel screen cathode and a Luggin capillary with a saturated calomel reference electrode (SCE). The cell was divided by a porous, ceramic cup into catholyte and anolyte compartments—to each of which was charged 100 grams of a 0.5 molar solution of $NaBF_4$ in 1/19 (by weight) water/$CH_3CN$. Ten grams of $ZnCl_2$, 10 grams of PCP and 16 grams of $NH_4OAc$ were present in the catholyte. The cell contents were heated to 78° C. and the cathode potentiostated at −1.3 volts (vs SCE) with a Brinkman Wenking HP72 potentiostat. The cell voltage required to establish the latter potential resulted in an average cell current of about 1.5 A (21 mA/cm$^2$ of cathode surface). During the ensuing reaction, an equivalent volume (3.8 ml) of c. hydrochloric acid was added slowly—at a rate based on % PCP conversion figures obtained with a Hewlett-Packard Model 1082B High Performance Liquid Chromatograph from successive samples of the catholyte. (The column used was a 10 cm, 5 micron, $C_{18}$ column eluted at 40° C. with 12.5% methanol/water and the appropriate detection wavelength was 300 nm.)

When 0.31 Faradays of current had been passed, 93% of the PCP had been converted to sym-tet and 1% to trichloropyridines, the other 6% being unconverted. The reaction mixture was concentrated. The concentrate was allowed to cool to room temperature and filtered. The filtrand—a mass of white sym-tet crystals—was water-washed and, after air drying, weighed 7.5 grams (87% of theoretical yield). The rest of the sym-tet which had formed could have been recovered from the filtrate, which included the unconverted pentachloropyridine, by fractional distillation.

The initial current efficiency was 50% and the average efficiency was 25%.

EXAMPLE 2

(No Acid Source Material Added and More Water Used)

The procedure of Example 1 was essentially repeated, except that no $NH_4OAc$ or HCl was added, the water content in the $CH_3CN$ was increased to 20% and the reaction was continued until 0.41 Faradays of current had passed through the cell. The PCP conversion was 95% (93% to sym-tet and 2% to trichloropyridines). The average current efficiency was 20%. The sym-tet was isolated in an 88% yield.

The conditions and results in the foregoing Examples are recapitulated in Table 1 following, together with the same data for several other experiments—run for purposes of comparison and not to illustrate the subject matter claimed in the present application. These latter experiments are numbered 3a through g in the Table.

TABLE 1

ELECTROCATALYTIC REDUCTION OF PCP TO SYM-TET WITH $ZN^{2+}$

| Example | Solvent | Other Catholyte Components | Temp (°C.) | Cathode Voltage (V vs SCE) | Initial Current Density (mA/cm$^2$) | Current Passed (Faradays) | Grams[2] PCP Charged | Current Efficiency (%) | % PCP Converted | % PCP Charged Converted to % Sym-Tet | % Tri's |
|---|---|---|---|---|---|---|---|---|---|---|---|
| 1 | $CH_3CN$ | $NaBF_4$ 51% $H_2O$ $ZnCl_2$ $NH_4OAc$ | 78 | −1.33 | 21 | 0.310 | 10 | 25 | 94 | 93 | 1 |
| 2 | $CH_3CN$ | $NaBF_4$ $ZnCl_2$ 20% $H_2O$[1] | 78 | −1.34 | 57 | 0.410 | 10 | 20 | 95 | 93 | 2 |
| 3a | $CH_3OH$ | $ZnCl_2$ 10% $H_2O$ | 65 | −1.70 | 26 | 0.35 | 5 | 10 | 88 | 71 | 11 |
| b | $CH_3OH$ | LiCl 10% $H_2O$ | 65 | −1.86 | 26 | 0.18 | 5 | — | 5 | — | — |
| c | Sulfolane[3] | $ZnCl_2$ $NH_4OAc$ 5% $H_2O$ | 90 | −1.65 | 66 | 0.048 | 5 | 65 | 80 | 73 | 3 |
| d | Sulfolane[4] | $ZnCl_2$ $NH_4OAc$ 50% $H_2O$ | 100 | −1.67 | 33 | 0.032 | 2 | 40 | 90 | 62 | 7 |
| 3e | DOWANOL-ME | $KBF_4$ 5% $H_2O$ $ZnCl_2$ $NH_4Cl$ | 100 | −1.30 | 26 | 0.04 | 5 | 36 | 37 | 32 | 3 |
| f | DOWANOL-ME | $KBF_4$ $NH_4Cl$ 5% $H_2O$ | 100 | −1.30 | 26 | 0.04 | 5 | 6 | 12 | 6 | 4 |
| g | Propylene[5] Carbonate | $NaPF_6$ $NH_4OAc$ $ZNCl_2$ | 120 | −1.30 | 26 | 0.26 | 10 | 22 | 74 | 71 | 3 |

NOTES
[1] 100 × grams $H_2O$ ÷ (grams $H_2O$ + 10); 10 grams solvent in each experiment.
[2] Grams PCP per 100 grams solvent/$H_2O$/$NaBF_4$.
[3] Silver cathode (unanodized).
[4] Stainless steel cathode.
[5] Rapid voltage rise occurred due to occluding of separator by deposition of apparently polymeric film.

What is claimed is:

1. The method of preparing 2,3,5,6-tetrachloropyridine which comprises electrocatalytically reducing pentachloropyridine at a cathode immersed in a catholyte comprising a solution of the pentachloropyridine, water and $ZnCl_2$ or $ZnBr_2$ in a solvent which is or has the essential characteristics of acetonitrile.

2. The method of claim 1 comprising:

a. providing an electrolytic cell having a cathode and an anode,
b. charging to said cell, as said catholyte, said solution, a non-basic supporting electrolyte, and, optionally, an acid source material,
c. charging to said cell as the anolyte a solution comprising a water-miscible solvent, water, a non-basic supporting electrolyte and, optionally, an acid source material,
d. heating the cell contents as necessary to establish the temperature within the range of from about 25° to about 100° C.,
e. applying across the cell a D.C. potential such as to establish and maintain a cathode potential of from about $-2$ to about $-1$ volts, for a period of time as required to attain a desired degree of conversion of the pentachloropyridine,
said anode consisting of an inert, electroconductive material at which $Cl^-$ and/or $Br^-$ ions can be oxidized to a halogen which is $Cl_2$, $Br_2$ or $BrCl$, or at which hydroxyl ions can be oxidized to water and $O_2$.

3. The method of claim 2 in which said electrolyte is a neutral or acidic salt.

4. The method of claim 2 in which said cell is a divided cell or is otherwise adapted to minimize reoxidation of the zinc and/or chloropyridine species.

5. The method of claim 2 in which the cathode material is stainless steel.

6. The method of claim 2 in which an acid source material is introduced to the catholyte and/or anolyte.

7. The method of claim 3 in which the electrolyte is $NaBF_4$, the solvent in the catholyte and anolyte is $CH_3CN$, the cell is divided and the cathode material is stainless steel.

8. The method of claim 7 in which an acid source material is introduced to the catholyte and/or anolyte.

9. The method of claim 8 in which the anode material is ruthenium oxide on titanium.

10. The method of claim 9 in the cathode potential is within the range of from about $-1.3$ to about $-1.4$ volts.

11. The method of any one of claims 3, 4, 5, 6, 7, 8, 9 or 10 in which the amount of water in the cell, relative to the amount of said solvents, is within the range of from about 5 to about 15 wt. %.

* * * * *